United States Patent
Lee

(10) Patent No.: US 9,526,848 B2
(45) Date of Patent: Dec. 27, 2016

(54) ANTI-NOCICEPTIVE APPARATUS

(71) Applicant: Choon Kee Lee, Denver, CO (US)

(72) Inventor: Choon Kee Lee, Denver, CO (US)

(*) Notice: Subject to any disclaimer, the term of this patent is extended or adjusted under 35 U.S.C. 154(b) by 773 days.

(21) Appl. No.: 13/936,182

(22) Filed: Jul. 6, 2013

(65) Prior Publication Data

US 2015/0011971 A1   Jan. 8, 2015

(51) Int. Cl.
*A61M 5/00* (2006.01)
*A61M 5/42* (2006.01)

(52) U.S. Cl.
CPC ................................ *A61M 5/422* (2013.01)

(58) Field of Classification Search
CPC .................................................. A61M 5/422
USPC .................. 604/112, 116, 22; 601/72, 78
See application file for complete search history.

(56) References Cited

U.S. PATENT DOCUMENTS

| | | | |
|---|---|---|---|
| 3,620,209 | A | 11/1971 | Kravitz |
| 6,231,531 | B1 | 5/2001 | Lum |
| 8,121,696 | B2 | 2/2012 | Vallero |
| 8,147,533 | B2 | 4/2012 | Baxter |
| 2007/0088385 | A1 | 4/2007 | Perry |
| 2008/0086063 | A1 | 4/2008 | Baxter |
| 2008/0086159 | A1 | 4/2008 | Zweifler |
| 2008/0255483 | A1 | 10/2008 | Goldberg |
| 2011/0022115 | A1 | 1/2011 | Salzhauer |
| 2011/0054386 | A1 | 3/2011 | Blaine |
| 2011/0288456 | A1 | 11/2011 | Vallero |
| 2011/0288471 | A1* | 11/2011 | Fallek ............. A61M 5/422 604/22 |
| 2012/0016292 | A1* | 1/2012 | Goldberg ........... A61H 7/005 604/22 |
| 2012/0179099 | A1 | 7/2012 | Baxter |

OTHER PUBLICATIONS

Giordano J: The neurobiology of nociceptive and antinociceptive systems. 2005; 8:277-290, Pain Physician. USA.
Hudspith MJ, Siddall PJ, and Munglani R: Physiology of pain. 2006. Foundations of anesthesia, second edition. Elsevier Mosby, NY, USA.
Charlton JE: Stimulation-produced analgesia. 2005. Core Curriculum for Professional Education in Pain. IASP Press, Seattle, USA.

(Continued)

*Primary Examiner* — Matthew F Desanto

(57) ABSTRACT

The present invention presents an apparatus and methods to generate and deliver resonant vibrations to a needle penetration site of a human body to reduce pain of needle prick by activating inhibitory neuronal mechanisms for pain perception. The apparatus comprises a longitudinal injector pen carriage assembly which releasably holds and slidably moves a proximal portion of an injector pen and a vibration assembly which generates and delivers vibrations to a vibration resonance enclosure located at a proximal end of the apparatus. The vibration assembly adjoins in parallel the injector pen carriage assembly. The injector pen with a needle moves forward in the injector pen carriage assembly along a longitudinal axis and the needle penetrates a recipient's tissue which is in direct contact with and is vibrated by the proximal end of the apparatus.

8 Claims, 4 Drawing Sheets

(56) References Cited

OTHER PUBLICATIONS

Smith KC, Comite SL, Balasubramanian S, Carver A, Liu JF; Vibration anesthesia: A noninvasive method of reducing discomfort prior to dermatologic procedures. Dermatology Online Journal 10 (2):1, USA.

Hollins M, Roy EA, Crane SA: Vibratory antinociception: Effects of vibration amplitude and frequency. Sep. 2003;4 (7):381-391. J Pain, Elsevier. NY, USA.

Zoppi M, Voegelin MR, Signorini M, Zamponi A: Pain threshold changes by skin vibratory stimulation in healthy subjects. Dec. 1991;143(4):439-443. Acta Physiol Scand, Wiley-Blackwell, NJ, USA.

Roy EA, Hollins M, Maixner W: Reduction of TMD pain by high-frequency vibration: a spatial and temporal analysis. Feb. 2003;101(3):267-274. Pain. Elsevier. NY, USA.

\* cited by examiner

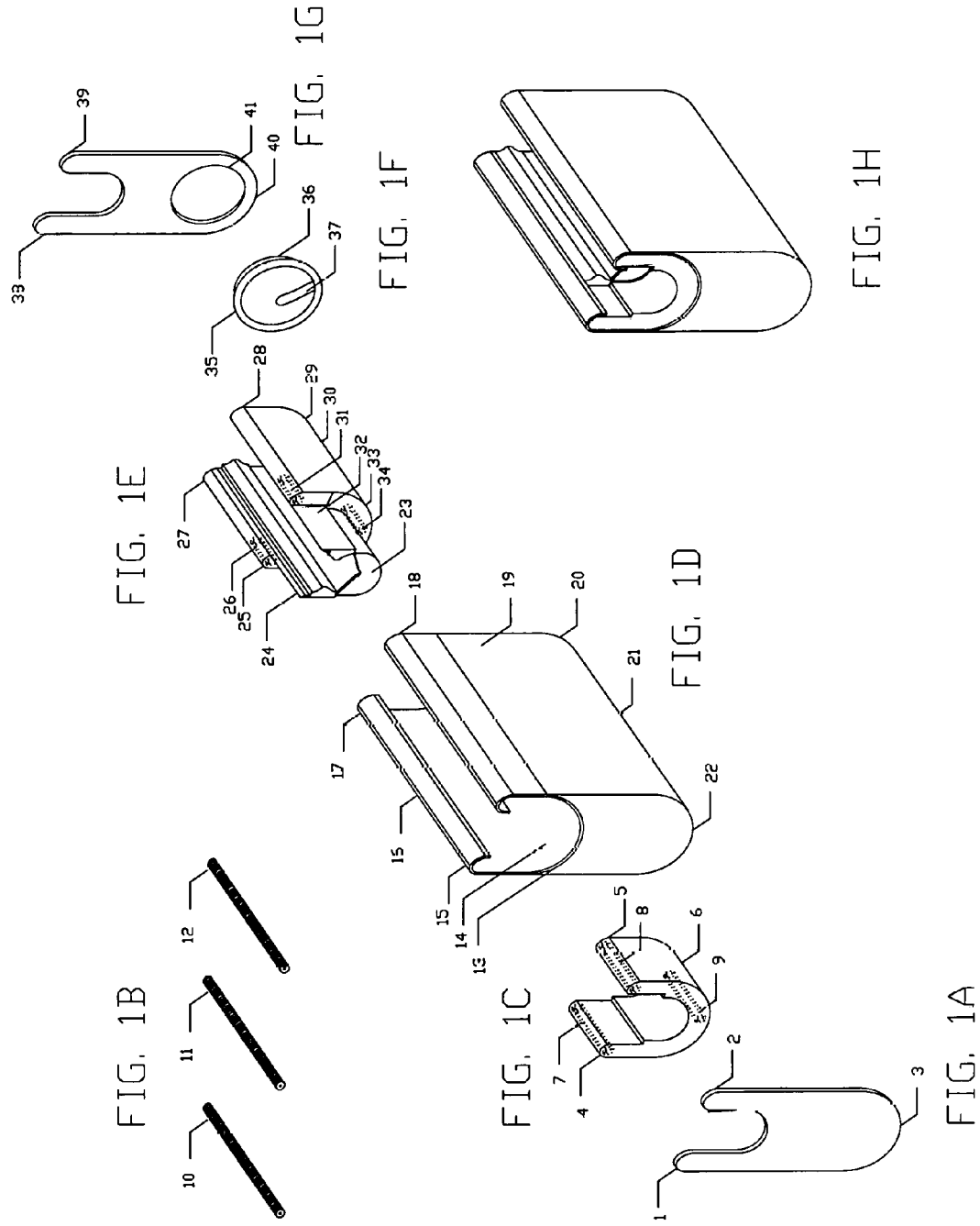

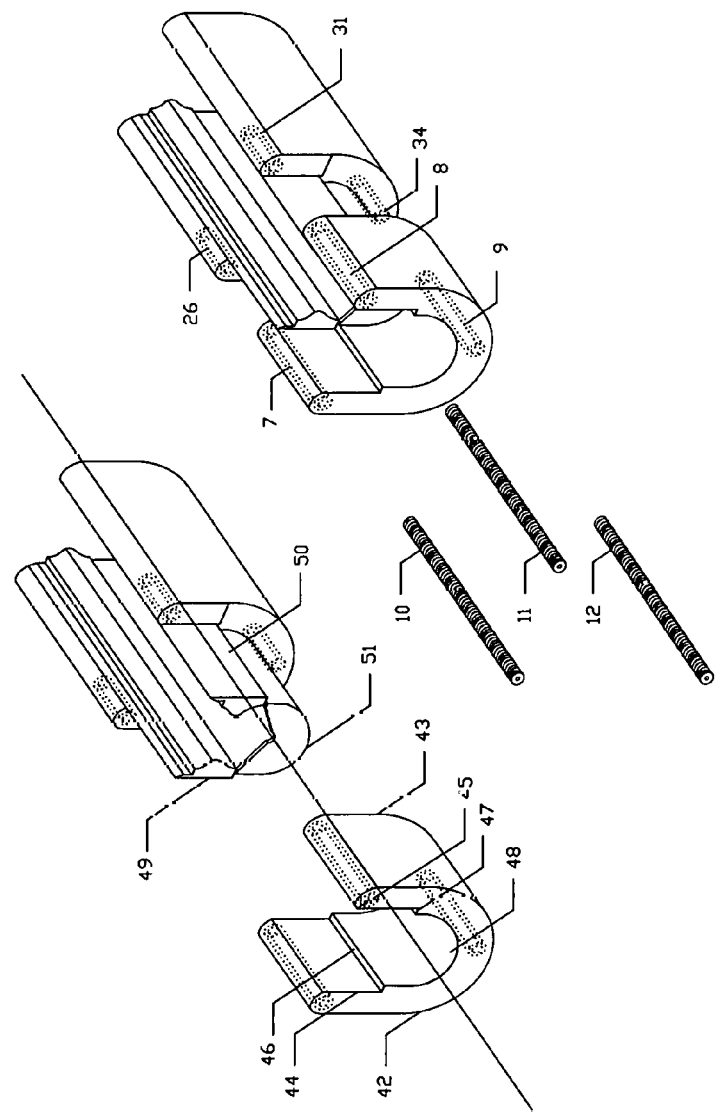

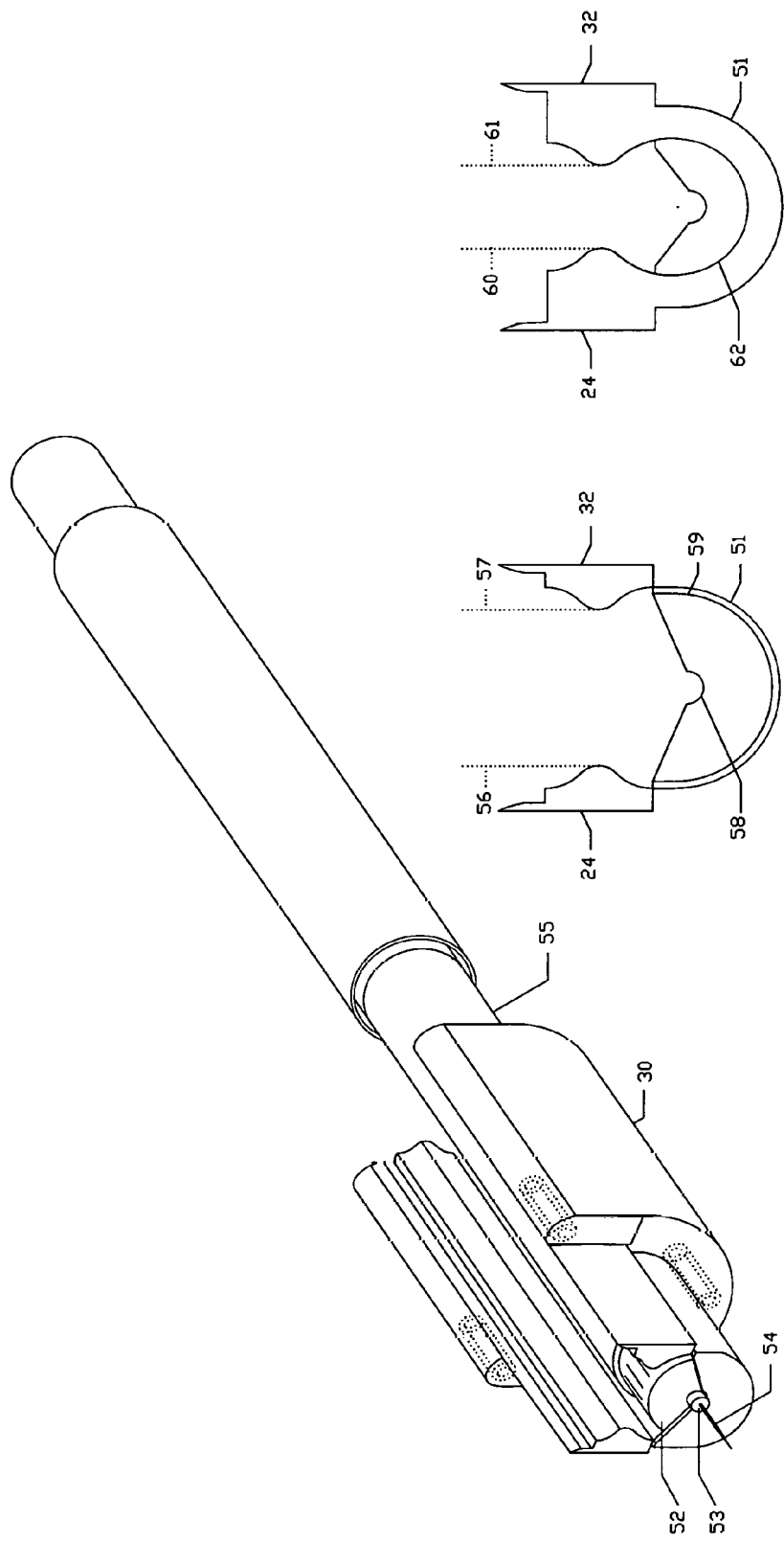

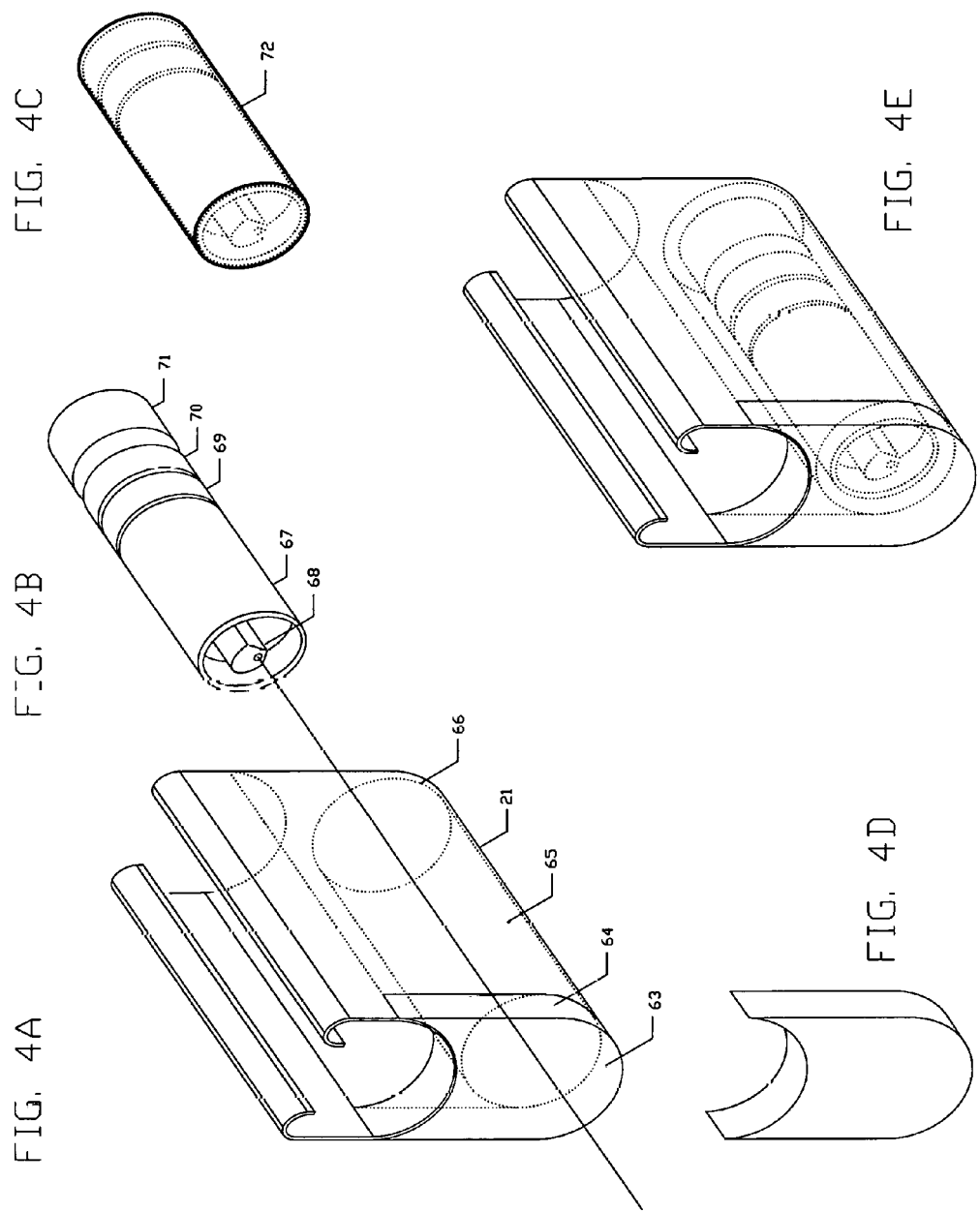

ANTI-NOCICEPTIVE APPARATUS

TECHNICAL FIELD

The present invention relates generally to the field of hypodermic injection of an agent for medical purpose. More specifically, the present invention provides an apparatus and methods to reduce pain and discomfort associated with an entry of a needle of an injector pen and an injectable agent into tissue.

BACKGROUND OF THE INVENTION

Injection of an agent into cutaneous and muscle tissues through a needle prick disrupts mechanical and chemical stability of the tissue and initiates a series of electrophysiological and biochemical cascade in the local tissue environment and in free nerve endings of nociceptive primary afferent nerve fibers embedded in the tissue. Cationic channels of the free nerve endings are activated, dependent on biophysical properties of both the needle prick and injected agent. Once voltage gated Na+ channels are activated, membrane depolarization of the nociceptor is propagated, resulting in release of intracellular Ca++. The increase in Ca++ concentration mediates cellular and microenvironmental changes to sensitize nociceptors of the free nerve endings. Furthermore, cells that are disrupted by needle prick could releasec membrane fatty acids which convert to prostaglandins. Increase in prostaglandins could intensify nociceptive response of the free nerve endings, which translates into intensified painful sensation by a subject.

The majority of the nociceptive signals generated by the free nerve endings are transmitted via both A-delta and C nerve fibers to superficial dorsal horn of the spinal cord. A-delta nerve fibers are responsible for initial sensation of sharp localized pain and C fibers are responsible for so-called second pain of burning and bruised feeling over a wider area than perceived by the A-delta fibers. A-delta fibers are known to be sensitized by intense heat, and high intensity and prolonged activation of C fibers are known to perpetuate the sensitization cycle of C fibers by producing ligands acting on release of pro-inflammatory molecules. At the spinal cord, both A-delta and C– fibers produce glutamate that is a key molecule for transmission of sensation of pain. Postsynaptic nociceptive input then travels upward from the spinal cord to various parts of brain.

There are inhibitory neuronal signals arising from various parts of the brain that descend in the spinal cord to modulate nociception. Descending inhibitory signals may be activated by external factors including stimulation on peripheral or central nervous system. In addition, there are ascending inhibitory signals, albeit minor, arising from parts of the brain. Descending inhibitory signals come to various neuronal structures of the dorsal horn of the spinal cord where downward postsynaptic changes inhibit nociceptive responses. It is believed that in human subjects the descending inhibitory signals can be physically activated by acupuncture, transcutaneous electric nerve simulation (TENS), vibration, dorsal column stimulation and deep brain stimulation.

Vibration is one of peripheral stimulation methods to reduce nociception, which include TENS, acupuncture, acupuncture-like TENS, electroacupuncture and acupressure. Exact mechanisms of analgesia induced by vibration have not been clarified yet but it is believed to be related to activation of A-beta primary afferent nerve fibers that inhibit segmental neurons of the dorsal horn of the spinal cord. It is also proposed that vibration stimulates both high-threshold A-beta fibers and A-delta fibers, which activates the descending inhibitory signals to suppress the dorsal horn neurons. Clinically, both TENS and vibration have been shown to reduce acute and chronic pain conditions, including low back pain, acute orofacial pain, causalgia, pain associated with vaginal delivery of baby and arthritic pain. In particular, vibration of cutaneous tissue of patients has been shown to reduce pain associated with needle prick and injection of agents into the tissue, thereby reducing requirement of anesthetic agents for minor procedures on skin and its appendages.

Various frequencies have been studied for vibration induced analgesia, ranging from 20 Hz to 300 Hz with a varying degree of effectiveness on analgesia. Additional issues of vibration such as duration, amplitude and effective area and depth under vibration have not been studied for its comparative effectiveness except that it appears that analgesia is achieved best in an area directly under vibration. Shortcomings of vibration are short duration of effects and potential development of tolerance over repetitive uses.

Intensity of nociception, i.e., pain sensation, associated with conventional hypodermic injection of an agent may be ameliorated by limiting extent of mechanical and chemical disruption of a target tissue and by activating descending inhibitory signals. Thinner and shorter hypodermic needles with a more acute angle of bevel may reduce the extent of mechanical disruption of the tissue. Stimulation of an injection site by vibration is one of available methods to activate the descending inhibitory signals. Successful implementation of vibration for achieving analgesia during the needle-based injection would require generation of a vibration field sufficiently wide enough to cover both a needle penetration site and a tissue infiltration site of an injected agent for an adequate length of time, adequate and redundant activation of primary afferent nerve fibers and fast diffusion of the injected agent from the tip of a needle to adjacent tissues.

SUMMARY OF THE INVENTION

To achieve on-site placement of vibration in close proximity to a needle penetration site of a recipient and to a tissue infiltration site of an injected agent as a single-user apparatus for an injector pen such as insulin pen, the current apparatus comprises a U-shaped longitudinal injector pen carriage assembly which releasably holds and slidably moves a proximal portion of the injector pen, and a vibration assembly which generates and delivers vibrations to a vibration resonance enclosure located at a proximal end of the apparatus. The vibration assembly adjoins in parallel the injector pen carriage assembly along a longitudinal axis of the apparatus and is reversibly activated by an electric power. The vibration assembly is connected proximally to the vibration resonance enclosure. The injector pen carriage assembly comprises a piuxiinal part and a distal part which slidably and reversibly is coupled with the proximal part in a longitudinal slide-rail configuration. The proximal end of the apparatus comprises a proximal end of the injector pen carriage assembly and a proximal end of the vibration resonance enclosure, and contacts a recipient's skin and is configured to provide substantially tangential vibration to a needle penetration site. A distal end of the apparatus comprises a button switch covering a distal end of the battery and an open U-shaped distal end of the injector pen carriage assembly which is aligned in parallel with said button switch.

In one embodiment, the apparatus is provided in one or a plurality of configurations to releasably hold and advance a proximal portion of an injector pen and to place a vibration assembly in a manner to deliver substantially tangential vibrations to a needle penetration site. In one example, the apparatus has a three-compartment configuration which comprises a U-shaped longitudinal injector pen carriage assembly, a cylindrical vibration assembly and a vibration resonance enclosure. In one of examples of various configurations, the U-shaped injector pen carriage assembly is cylindrically half-tubular, which has a longitudinally linear opening on a side of said cylindrical half-tube. The longitudinally linear opening forms an open inlet of the U-shaped injector pen carriage assembly which allows the proximal portion of the injector pen to be securely and releasably inserted in a U-shaped gronve inside said U-shaped injector pen carriage assembly. The U-shaped injector pen carriage assembly comprises a U-shaped rail portion located proximally, a U-shaped slide portion located distally and a U-shaped housing which longitudinally encases both the rail and slide portions. Both the rail and slide portions are coaxial and reversibly engage with each other along the longitudinal axis.

In one embodiment, the U-shaped slide portion has a proximal part comprising a cylindrical half-tubular portion having an adjoining vertical sidewall on each free lateral border and a flat semicircular wall fixedly attached at a right angle to a proximal end of said cylindrical half-tube and a distal part having a cylindrical half-tubular shaft without a closing wall at a distal end. The flat semicircular wall has a central notch to accommodate and releasably hold a needle hub of a needle cap. A radius of the proximal cylindrical half-tube of said slide portion is smaller than that of the distal cylindrical half-tube of said slide portion, which is configured to let said proximal cylindrical half-tube reversibly slide in and out of the U-shaped rail portion along the longitudinal axis. An inner wall of the cylindrical half-tubular portion has a longitudinal ridge along each lateral border of said inner wall to securely hold and reversibly release the proximal portion of the injector pen. Both the cylindrical half-tubular portion and longitudinal ridges are provided in a range of cross-sectional thickness and radius to accommodate injector pens of various cross-sectional diameters. Both the vertical sidewalls and an outer wall of the cylindrical half-tubular portion of the proximal part are configured to slide in and out of the U-shaped rail portion.

In one embodiment, the U-shaped rail portion is provided in a U-shaped groove configuration similar to the distal part of the U-shaped slide portion. An inner wall of a vertical rail of the U-shaped rail portion has a horizontal rail on each vertical rail along the longitudinal axis, on which the vertical sidewall of the prnximal part of the U-shaped slide portion slides. The inner wall of the vertical rail of the U-shaped rail portion matches an outer wall of the vertical sidewall of the U-shaped slide portion. An inner wall of a bottom of the U-shaped rail portion matches the outer wall of the cylindrical half-tubular portion of the proximal part of the U-shaped slide portion. The U-shaped rail portion is fixedly attached to the outer housing whereas the U-shaped slide portion is slidable inside said housing. In one embodiment, the U-shaped rail portion has a plurality of longitudinal tubular spaces for compression spring in the wall. Each tubular space of the U-shaped rail portion matches a corresponding tubular space of the U-shaped slide portion, in both of which a single compression spring is placed along a longitudinal axis of said tubular space.

In one embodiment, the vibration assembly, provided as one or a plurality of operating devices having one or a plurality of mechanical configurations, comprises a vibration generator, a control electronics and a power source, and is housed in a longitudinally cylindrical enclosure which is connected proximally to the vibration resonance enclosure located at the proximal end of the apparatus. The cylindrical enclosure is provided in one or a plurality of configurations, including a cylindrical tube having a closed proximal end and an open distal end. An inner surface of the cylindrical enclosure is covered with one or a plurality of electromagnetic field-shielding materials such as copper or aluminum to reduce exposure of an operator's hand to the electromagnetic field. Vibrations in one or a plurality of frequencies ranging from 20 Hz to 20 kHz are produced by a vibratory motor provided in one or a plurality of electromechanical configurations including an eccentric mass rotary motor or by an electromagnetic disc vibrator. Frequency of the vibration is controllable by rotational speed of the vibratory motor. A higher rotational speed of the vibratory motor produces a higher frequency and a lower rotational speed of the motor produces a lower frequency. The control electronics is provided in one or a plurality of electronic configurations, which comprises an electronic circuit board and is connected to the power source and to a button switch located at the distal end of the apparatus. The control electronics controls an electric current to the vibration generator and modulates frequencies of vibrations. The power source includes one or a plurality of replaceable or rechargeable batteries and is electrically connected to the control electronics and to the button switch.

In one embodiment, the vibration resonance enclosure has a proximal end which contacts a recipient's tissue and delivers vibrations, a distal end which is attached to the vibration generator and transmits vibrations to said vibration resonance enclosure and a resonance chamber connecting both the proximal and distal ends The vibration resonance enclosure provides resonance which amplifies vibration in a certain range of frequencies generated by the vibration generator. One of the configurations of the vibration resonance enclosure provides a natural frequency of said resonance matched to a frequency range from 20 Hz to 300 Hz.

In one embodiment, a proximal portion of an injector pen is inserted in the U-shaped groove of the U-shaped injector pen carriage assembly, with a needle hub resting on the central notch of the proximal cylindrical half-tube and the needle cap attached to the proximal end of the injector pen placed firmly against an inner wall of the flat semicircular wall of the proximal part of the U-shaped slide portion. The injector pen is secured by a pair of longitudinal ridges of the inner wall and by the inner wall of the cylindrical half-tube of the distal part of the U-shaped slide portion. The button switch at the distal end of the apparatus is pushed in to generate vibrations and the apparatus is placed firmly against a tissue of a recipient. The injector pen is then manually pushed forward along the longitudinal axis, which slides forward the proximal part of the U-shaped slide portion in the U-shaped rail portion to the proximal end of said U-shaped rail portion. The forward push of the injector pen compresses the compression springs in the tubular spaces of both the U-shaped slide and rail portions. The needle of the injector pen penetrates the recipient's tissue and delivers an injectable agent. Once the forward push is released following completion of the injection, the compression springs in the tubular spaces extend back to push the U-shaped slide portion back to the original position. The injector pen is manually released, thereby completing one full cycle of injection. Following removal of the injector pen, the button switch is pushed again to break the electric connection for the vibrations. In one embodiment, the button switch turns on and off the vibration assembly and directs the electronic circuit board to vary frequencies of vibrations by a plurality of pre-set numbers of push-to-make and push-to-break actions on said switch.

In one embodiment, the apparatus is configured to be washable and sterilizable. The vibration assembly is provided in one or a plurality of configurations for release as a single unit from the cylindrical enclosure of the apparatus. The apparatus comprises the compression springs made of stainless spring steel which prevents rusting of said springs and one or a plurality of chemical- and heat-tolerant polymers which do not deform at high temperatures above 60° C. The distal end of the apparatus comprises a removable rear panel which allows the vibration assembly, a battery and the button switch to be removed from said apparatus. Following the removal of said devices, remaining components of the apparatus are washable and sterilizable by boiling water, autoclaving, bleaching or wiping by alcohol.

BRIEF DESCRIPTION OF THE DRAWINGS

FIGS. 1A-1H show an exploded view of an schematic example of itemized components of the apparatus: FIG. 1A represents a front panel; FIG. 1B represents a set of compression springs; FIG. 1C shows a U-shaped rail portion of the injector pen carriage assembly; FIG. 1D shows a main body; FIG. 1E shows a U-shaped slide portion of the injector pen carriage assembly; FIG. 1F shows a button switch; FIG. 1G shows a rear panel; FIG. 1H shows a fully assembled apparatus except for the front panel to illustrate a contour of the individual components at the proximal end.

FIGS. 2A-2C show a schematic example of individual parts of the injector pen carriage assembly: FIG. 2A represents an example of unassembled U-shaped rail and slide portions; FIG. 2B shows the U-shaped rail portion assembled with the U-shaped slide portion; FIG. 2C shows the U-shaped slide portion proximally slid in a matching U-shaped groove of the U-shaped rail portion.

FIGS. 3A-3C show a schematic example of the U-shaped slide portion of the injector pen carriage assembly: FIG. 3A shows an example of a placement of the injector pen in the U-shaped slide portion; FIGS. 3B and 3C show a cross-sectional view of the U-shaped groove in varying cross-sectional thicknesses and radii.

FIGS. 4A-4E show a schematic example of vibration compartments of the main body of the apparatus; FIG. 4A represents an overview of the vibration compartments; FIG. 4B shows a vibration assembly; FIG. 4C shows a cylindrical enclosure of the vibration assembly; FIG. 4D shows an example of a vibration resonance enclosure; FIG. 4E shows an example of assembled components in the vibration compartments.

DETAILED DESCRIPTION OF THE DRAWINGS

As described below, the present invention provides a vibration analgesia apparatus and methods of use. It is to be understood that the descriptions are solely for the purposes of illustrating the present invention, and should not be understood in any way as restrictive or limited. Embodiments of the present invention are preferably depicted with reference to FIGS. 1 to 4, however, such reference is not intended to limit the present invention in any manner. The drawings do not represent actual dimension of devices, but illustrate the principles of the present invention.

FIGS. 1A-1H show an exploded view of an schematic example of itemized components of the apparatus. FIG. 1A shows a pair of top edges 1 and 2 and a base 3 of a front panel which fixedly covers a proximal end of a U-shaped rail portion of FIG. 1C and a proximal end of a main body of FIG. 1D. The front panel contacts a tissue of a recipient and the base 3 transmits substantially tangential vibrations to a needle penetration site of a tissue bordered by both the top edges 1 and 2. FIG. 1B shows a set of compression springs 10-12 which are configured to be placed in a set of tubular spaces 7-8 of the U-shaped rail portion of FIG. 1C and in a corresponding set of tubular spaces 26, 31 and 34 of a U-shaped slide portion of FIG. 1E. FIG. 1C shows a proximal end 4 and a distal end 5 of the U-shaped rail portion, which are connected by a U-shaped base 6. The U-shaped rail portion of FIG. 1C fixedly is placed inside a U-shaped housing 13 of the main body of FIG. 1D, with the proximal end 4 vertically aligned with a proximal end 15 of an inverted J-shaped groove 16 and an outer wall of the base 6 enclosed by a floor 14 of the U-shaped housing. A base 22 of a proximal end of the main body of FIG. 1D irreversibly adheres to the base 3 of the front panel of FIG. 1A.

A proximal part of the U-shaped slide portion of FIG. 1E comprises a cylindrical half-tube with a semicircular front wall 23 and a pair of vertical slides 24 and 32. A distal part of the U-shaped slide portion comprises a proximal end with a pair of top edges represented as 25 for one side and a base 33, a distal end with a pair of top edges 27 and 28 and a base 29, and a mid portion base 30 connecting both the proximal and distal ends. The U-shaped slide portion of FIG. 1E movably is encased in the U-shaped housing 13 of the main body, with the top edges 27 and 28 of the distal end vertically aligned with a corresponding inverted J grooves 17 and 18 of the distal end of the main body. Both the distal ends of the U-shaped slide portion and the main body are removably covered by a rear panel of FIG. 1G, with a base 40 of the rear panel attached to a base 20 of the distal end of the main body and a pair of top edges 38 and 39 attached to the corresponding top edges 27 and 28 of the main body. A mid portion base 21 of the main body connects the base 20 of the distal end to the base 22 of the proximal end, which houses a cylindrically tubular space for a vibration assembly.

The rear panel of FIG. 1G has an opening 41 through which an outer portion 36 of a button switch of FIG. 1F protrudes. The button switch releasably is anchored in front of the rear panel by an inner rim 35 and has an electric connection to a battery by a battery electrode 37. The button switch operates in a push-to-make and push-to-break manner to turn on and to turn off the electric connection, respectively. FIG. 1H shows a fully assembled apparatus except for the front panel to illustrate a contour of the proximal end of the individual components.

FIGS. 2A-2C show a schematic example of individual parts of the injector pen carriage assembly. FIG. 2A represents an example of the U-shaped rail portion which comprises a proximal end 42 and a distal end 43 of the U-shaped half-tube, a pair of vertical rails 44 and 45, a pair of horizontal rails 46 and 47 and a U-shaped floor rail 48. The U-shaped slide portion is coaxially aligned with the U-shaped rail portion and has a pair of lateral slides 49 and 50 matching the vertical rails 44 and 45, respectively, and an outer wall 51 of the cylindrical half-tube matching said U-shaped floor rail 48. FIG. 2B shows the U-shaped rail portion assembled with the U-shaped slide portion. Compression springs 10, 11 and 12 are inserted in a pair of tubular spaces 7 and 26, 8 and 31 and 9 and 34, respectively. FIG. 2C shows the U-shaped slide portion proximally slid in the matching U-shaped groove of the U-shaped rail portion to a full length.

FIG. 3A shows a schematic example of the U-shaped slide portion which holds a proximal part of the injector pen in the U-shaped groove. A needle cap 52 is positioned in the most proximal part of said U-shaped slide portion, along with a needle hub 53 and a needle 54. A part of an injector pen barrel 55 is inserted in said U-shaped groove of said U-shaped slide portion. Shown in FIGS. 3B and 3C of a cross-sectional view of the U-shaped groove, the injector pen barrel 55 is snugly secured by a pair of longitudinal ridges 56 and 57, with each running on an inner wall of said U-shaped slide portion for a length, and by an inner wall 59 of the cylindrical half-tube. A central notch 58 is configured to releasably hold the needle hub 53. An injector pen barrel of a smaller diameter requires an increase in cross-sectional thickness of the longitudinal ridges of the U-shaped groove, as represented as 60 and 61, and a smaller radius of the inner wall of the cylindrical half-tube, as depicted as 62.

FIGS. 4A-4E show a schematic example of vibration compartments of the main body 21 of the apparatus. FIG. 4A shows a proximal end 64 and a distal end 66 of a cylindrical enclosure 65 for a vibration assembly which is proximally attached to a vibration resonance enclosure 63. An inner surface of the cylindrical enclosure 65 is covered with one or a plurality of electromagnetic field-shielding materials such as copper or aluminum to reduce exposure of an operator's hand to the electromagnetic field. FIG. 4B shows a battery 71 and components of the vibration assembly, comprising an eccentric mass rotary vibration motor 67 having an eccentric mass 68 attached to a central rod of said motor, a vibration motor holder 69 and an electronic circuit board 70. The entire components of the vibration assembly except the battery are enclosed by a water resistant cylindrical shrink wrap 72, as shown in FIG. 4C, which allows said vibration assembly to be releasable as a single unit from the cylindrical enclosure 65. The vibration resonance enclosure 63 is provided in one or a plurality of configurations having a resonant chamber inside, as illustrated in FIG. 4D. Vibrations generated by rotational movements of the eccentric mass rotary motor 67 are transmitted to the vibration resonance enclosure 63. Referring to FIG. 1A, the vibration resonance enclosure 63 amplifies vibrations of a range of frequencies and transmits the resonated vibrations to the front panel. The front panel in FIG. 1A then transmits the vibrations to a tissue of a recipient. FIG. 4E shows an example of assembled components in the vibration compartments.

It is to be understood that the aforementioned description of the apparatus and methods is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. An anti-nociceptive apparatus, comprising:
   a vibration assembly, adjoining in parallel an injector pen carriage assembly;
   the vibration assembly, provided in a cylindrical configuration, wherein the vibration assembly comprising a vibration motor and an electronic circuit board is water resistant by a water resistant cylindrical polymer shrink wrap sealing said vibration assembly, wherein the vibration assembly is enclosed by an electromagnetic field-shielding cylindrical enclosure, wherein the vibration assembly is configured to deliver vibrations to a recipient's tissue via a vibration resonance enclosure located proximally to and in contact with said vibration assembly at a right angle; and
   the injector pen carriage assembly, provided in a collapsible configuration along a longitudinal axis of said injector pen carriage assembly, wherein the injector pen carriage assembly comprises an U-shaped rail portion slidably and coaxially assembled with an U-shaped slide portion located distally to said U-shaped rail portion, wherein the U-shaped slide portion is configured to coaxially slide to and fro in the U-shaped rail portion for a distance, wherein the U-shaped slide portion is configured to reversibly hold a proximal portion of the injector pen, wherein a proximal end of the U-shaped slide portion is configured in a three-quartered circle so as to provide an open cradle for a needle of the injector pen, and wherein the U-shaped slide and rail portions are insertably housed in a U-shaped outer housing.

2. The anti-nociceptive apparatus according to claim 1, wherein the vibration resonance enclosure comprises a rectangular resonant chamber configured in an enclosed rectangular box, wherein the vibration resonance enclosure is located at a proximal end of said anti-nociceptive apparatus, wherein the vibration resonance enclosure is configured to adjoin a proximal portion of the U-shaped outer housing, wherein an outer surface of a proximal wall of the vibration resonance enclosure is configured to contact a skin of the tissue so as to deliver the vibrations emanating from the vibration assembly, wherein a distal wall of the vibration resonance enclosure is configured to contact with a proximal end of the vibration assembly so as to transmit the vibration from the vibration assembly to the rectangular resonant chamber of said vibration resonance enclosure, and wherein the rectangular resonant chamber is configured to reflect the vibrations from the vibration assembly on an inner surface of said rectangular resonant chamber so as to amplify said vibrations.

3. The anti-nociceptive apparatus according to claim 1, wherein the injector pen carriage assembly comprises:
   the U-shaped slide portion, wherein the U-shaped slide portion comprises a proximal portion and a distal portion, wherein the proximal portion of the U-shaped slide portion comprises a proximal portion of a first vertical lateral slide, a proximal portion of a second vertical lateral slide located opposite to the proximal portion of said first vertical lateral slide, a U-shaped floor adjoining a bottom of the proximal portion of the first and the second vertical lateral slides along the longitudinal axis, and the proximal end configured in the three-quartered circle adjoining a proximal end of the proximal portion of the first and the second vertical lateral slides, wherein the proximal portion of the first and the second vertical lateral slides is configured to coaxially slide in the U-shaped rail portion to and fro, wherein the distal portion of the U-shaped slide portion comprises a distal portion of the first vertical lateral slide, a distal portion of the second vertical lateral slide located opposite to said first vertical lateral slide, a U-shaped floor adjoining a bottom of the distal portion of the first and the second vertical lateral slides along the longitudinal axis, an U-shaped outer wall fixedly attached to an outer surface of the distal portion of the first and the second vertical lateral slides and an outer surface of the U- shaped floor, wherein the first and the second vertical lateral slides are configured to reversibly hold the injector pen in a tubular configuration, and wherein the U-shaped slide portion is configured to slide to and fro in the U-shaped outer housing;

the U-shaped rail portion, wherein the U-shaped rail portion comprises a first vertical lateral rail, a second vertical lateral rail located opposite to the first vertical lateral rail, and an U-shaped floor rail adjoining the first and the second vertical lateral rails at a bottom of the first and the second vertical lateral rails along the longitudinal axis, wherein a junction between the bottom of the vertical lateral rail and the U-shaped floor rail is configured to form a horizontal rail so as to let the proximal portion of the vertical lateral slide of the U-shaped slide portion slide on the horizontal rail to and fro, wherein an outer surface of the U-shaped rail portion is fixedly attached to an inner wall of the U-shaped outer housing;

a plurality of compression springs, provided as a stainless steel compression spring, wherein a proximal end of a compression spring is inserted in a tubular space distally located in a wall of the U-shaped rail portion, wherein a distal end of the compression spring is inserted in a tubular space proximally located in the U-shaped outer wall of the distal portion of the U-shaped slide portion, wherein the compression spring is configured to separate the U-shaped rail portion from the U-shaped slide portion by a distance in an uncompressed configuration of the compression spring, and wherein the compression spring is configured to collapsibly let the proximal end of the U-shaped slide portion abut a proximal end of the U-shaped rail portion in a filly compressed configuration of the compression spring; and the U-shaped outer housing, wherein the U-shaped outer housing comprises a first vertical sidewall oppositely located to a second vertical sidewall, and an U-shaped floor adjoining a bottom of the first and the second vertical sidewalls, wherein the vertical sidewall comprises a groove configured in an inverted J so as to accommodate an upper portion of the vertical lateral rail of the U-shaped rail portion and an upper portion of the U-shaped outer wall of the distal portion of the U-shaped slide portion, wherein a proximal portion of the U-shaped floor of the U-shaped outer housing is configured to adjoin the vibration resonance enclosure, and wherein a mid portion and a distal portion of the U-shaped outer housing is configured to adjoin the electromagnetic field-shielding cylindrical enclosure enclosing the vibration assembly.

4. The anti-nociceptive apparatus according to claim 3, wherein the U-shaped slide portion of the injector pen carriage assembly in the uncompressed configuration of the compression springs of said injector pen carriage assembly is configured to hold the proximal portion of the injector pen in a way the needle of the injector pen is protected inside the U-shaped rail portion, wherein the U-shaped slide portion of the injector pen carriage assembly in the fully compressed configuration of the compression springs of said injector pen carriage assembly is configured to let the needle of the injector pen protrude from the proximal end of the U-shaped rail portion.

5. A method for reducing pain and discomfort associated with an entry of a needle of an injector pen comprising:
providing the anti-nociceptive apparatus of claim 3,
securing a proximal portion of an injector pen in the U-shaped slide portion of the injector pen carriage assembly;
placing a proximal end of the vibration resonance enclosure on a skin of a tissue of a recipient;
pushing a distal portion of the injector pen toward the skin of the tissue of the recipient;
compressing compression springs in an uncompressed configuration disposed in corresponding tubular spaces of the U-shaped rail portion and of the U-shaped slide portion so as to slide the U-shaped slide portion toward the U-shaped rail portion; and
releasing the distal portion of the injector pen from a pushed configuration so as to uncompress the compression springs from a compressed configuration and to retract the proximal portion of the injector pen from the skin of the tissue of the recipient.

6. The anti-nociceptive apparatus according to claim 1, wherein the anti-nociceptive apparatus is made of a plurality of chemical- and heat-tolerant polymers, wherein the vibration assembly of the anti-nociceptive apparatus is configured to be detachably removable from the electromagnetic field-shielding cylindrical enclosure of the anti-nociceptive apparatus so as to let a remaining part of the anti-nociceptive apparatus be washable and sterilizable.

7. The anti-nociceptive apparatus according to claim 1, wherein the electromagnetic field-shielding cylindrical enclosure comprises a cylindrical outer wall fixedly attached to a proximal sidewall and an openable distal lid configured to reversibly and tightly close a distal end of the electromagnetic field-shielding cylindrical enclosure, and wherein an inner surface of the cylindrical outer wall, of the proximal sidewall and of the openable distal lid is adherently coated by an electromagnetic field-shielding material so as to shield an electromagnetic field emanating from the vibration assembly.

8. A method for washing and sterilizing an anti-nociceptive apparatus comprising:
providing an anti-nociceptive apparatus comprising a vibration assembly, adjoining in parallel an injector pen carriage assembly; the vibration assembly, provided in a cylindrical configuration, wherein the vibration assembly comprising a vibration motor, a battery, and an electronic circuit board is water resistant by a water resistant cylindrical polymer shrink wrap sealing said vibration assembly, wherein the vibration assembly is enclosed by an electromagnetic field-shielding cylindrical enclosure, wherein the vibration assembly is configured to deliver vibrations to a recipient's tissue via a vibration resonance enclosure located proximally to and in contact with said vibration assembly at a right angle; and the injector pen carriage assembly, provided in a collapsible configuration along a longitudinal axis of said injector pen carriage assembly, wherein the injector pen carriage assembly comprises an U-shaped rail portion slidably and coaxially assembled with an U-shaped slide portion located distally to said U-shaped rail portion, wherein the U-shaped slide portion is configured to coaxially slide to and fro in the U-shaped rail portion for a distance, wherein the U-shaped slide portion is configured to reversibly hold a proximal portion of the injector pen, wherein a proximal end of the U-shaped slide portion is configured in a three-quartered circle so as to provide an open cradle for a needle of the injector pen, and wherein the U-shaped slide and rail portions are insertably housed in a U-shaped outer housing;

removing the vibration assembly and the battery from the electromagnetic field- shielding cylindrical enclosure;

washing the anti-nociceptive apparatus without the vibration assembly and the battery with a soap;

drying the anti-nociceptive apparatus without the vibration without the vibration assembly and the battery; and sterilizing the anti-nociceptive apparatus without the vibration assembly and the battery.

* * * * *